US006553680B2

(12) United States Patent
Vazdi

(10) Patent No.: US 6,553,680 B2
(45) Date of Patent: Apr. 29, 2003

(54) DEVICE FOR PLACING NON-PERMANENT LINES ON THE FACE

(76) Inventor: Kamran Vazdi, 10535 Wilshire Blvd., #905, Los Angeles, CA (US) 90024

( * ) Notice: Subject to any disclaimer, the term of this patent is extended or adjusted under 35 U.S.C. 154(b) by 0 days.

(21) Appl. No.: 09/906,241

(22) Filed: Jul. 16, 2001

(65) Prior Publication Data

US 2003/0009896 A1 Jan. 16, 2003

(51) Int. Cl.[7] .............................................. G01C 15/02
(52) U.S. Cl. ........................................... 33/512; 33/286
(58) Field of Search ......................... 33/227, 228, 286, 33/1 BB, 1 CC, 512, DIG. 21

(56) References Cited

U.S. PATENT DOCUMENTS

| | | | | |
|---|---|---|---|---|
| 556,693 A | * | 3/1896 | Quimby ...................... 313/113 |
| 1,567,011 A | * | 12/1925 | Parziale ...................... 132/214 |
| 2,638,532 A | * | 5/1953 | Brady ...................... 280/438.1 |
| 3,060,308 A | * | 10/1962 | Fortuna ...................... 351/158 |
| 3,592,525 A | * | 7/1971 | Schultz ...................... 351/158 |
| 3,613,694 A | * | 10/1971 | Benjamin ...................... 132/145 |
| 3,709,234 A | * | 1/1973 | Seerahn ...................... 132/214 |
| 4,010,764 A | * | 3/1977 | Wagner ...................... 132/214 |
| 4,254,451 A | * | 3/1981 | Cochran, Jr. ................. 315/323 |
| 4,283,127 A | * | 8/1981 | Rosenwinkel et al. ......... 2/426 |
| 4,396,259 A | * | 8/1983 | Miller ......................... 351/158 |
| 4,938,582 A | * | 7/1990 | Leslie ......................... 351/158 |
| 5,182,585 A | * | 1/1993 | Stoner ......................... 351/158 |
| 5,383,280 A | * | 1/1995 | McDermott .................. 33/361 |
| 5,539,990 A | * | 7/1996 | Le ............................... 33/281 |
| 5,715,337 A | * | 2/1998 | Spitzer et al. ............... 359/209 |
| 5,946,071 A | * | 8/1999 | Feldman ...................... 351/158 |
| 6,195,902 B1 | * | 3/2001 | Jan et al. ....................... 33/286 |

* cited by examiner

Primary Examiner—Diego Gutierrez
Assistant Examiner—Madeline Gonzalez

(57) ABSTRACT

A device for placing one or more reference lines on the face of a user in such manner as not to mark the face in any manner. The device utilizes a frame adapted to rest on top of the nasal bone and the ears of the user. At least one line drawing attachment is detachably secured to the frame. The attachment includes an elongated hollow cylinder having an elongated slot extending from the interior to the exterior of the cylinder. The cylinder contains an elongated light source which when electrically energized projects a reference line of light through said slot.

4 Claims, 3 Drawing Sheets

DEVICE FOR PLACING NON-PERMANENT LINES ON THE FACE

BACKGROUND OF THE INVENTION

This apparatus employs one or more light sources to place non-permanent reference lines on the face for such purposes as placing the lower edges of opposite side burns at the same level, symmetrically fitting a mustache, properly trimming a beard or goatee and the like. The apparatus can be used for determining facial symmetry and anatomy and indeed for any purpose having to do with facial features.

SUMMARY OF THE INVENTION

In accordance with the principles of this invention, the device is used to place one or more reference lines on the face of a user in such manner as not to mark the face in any manner.

The device utilizes a frame adapted to rest on top of the nasal bone and the ears of the user. At least one line drawing attachment is detachably securable to the frame. The attachment includes one or more elongated hollow cylinders, each cylinder having an elongated slot extending from the interior to the exterior of the cylinder. Each cylinder contains an elongated light source which when electrically energized projects a reference line of light through said slot. The device further includes first means connected each source to energize it and produce the desired line or lines of light.

In use, the frame is placed on the face like a pair of glasses. The attachment or attachments as explained in more detail below can be secured to the frame in any position desired.

The line or lines are projected onto the face of the user as desired for the purposes indicated. Once the desired purpose is achieved, each source is deenergized and the line or lines disappear.

The frame has oppositely disposed horizontal ear pieces and a horizontal nose piece extending between and secured to said ear pieces. The pieces and each attachment have second cooperating engagement means which enable the attachment to engage any piece with the cylinder extending horizontally whereby said reference line extends horizontally and which also enable the attachment to engage any piece with the cylinder extending vertically whereby the reference line extends vertically.

Each attachment has third manually rotatable means secured to the cylinder to rotate it into different selected positions about its axis of elongation in a horizontal plane, thereby moving the reference line of light up or down in said horizontal plane.

Each attachment has fourth means for manually rotating the cylinder into different selected inclined positions in a vertical plane, thereby moving the reference line of light into corresponding inclined positions in said vertical plane.

The pieces can have holes and each attachment has prongs detachably engagable with said holes to enable each attachment to be engaged with the frame in any desired position.

The invention will now be described in more detail with reference both to the drawings and detailed descriptions which follow.

DETAILED DESCRIPTION OF PREFERRED EMBODIMENTS

Figure 1:
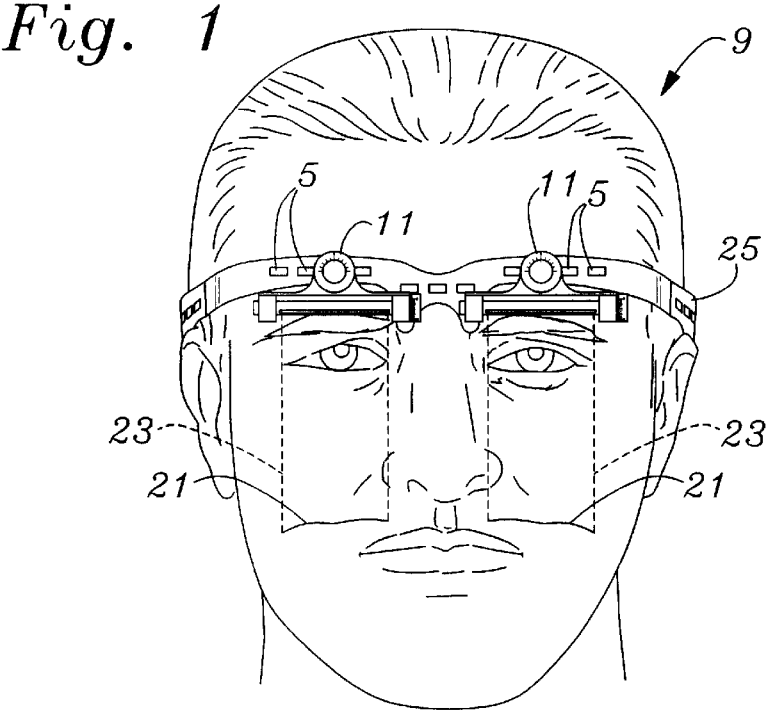
FIG. 1 is a front view of a preferred embodiment of the invention in use illustrating as an example possible alignment of both sides of a mustache.

Referring first to FIG. 1, head 9 supports frame 25 having slots 5, first and second light means 11 producing non-permanent light lines 21 having outside edges 23.

Figure 2:
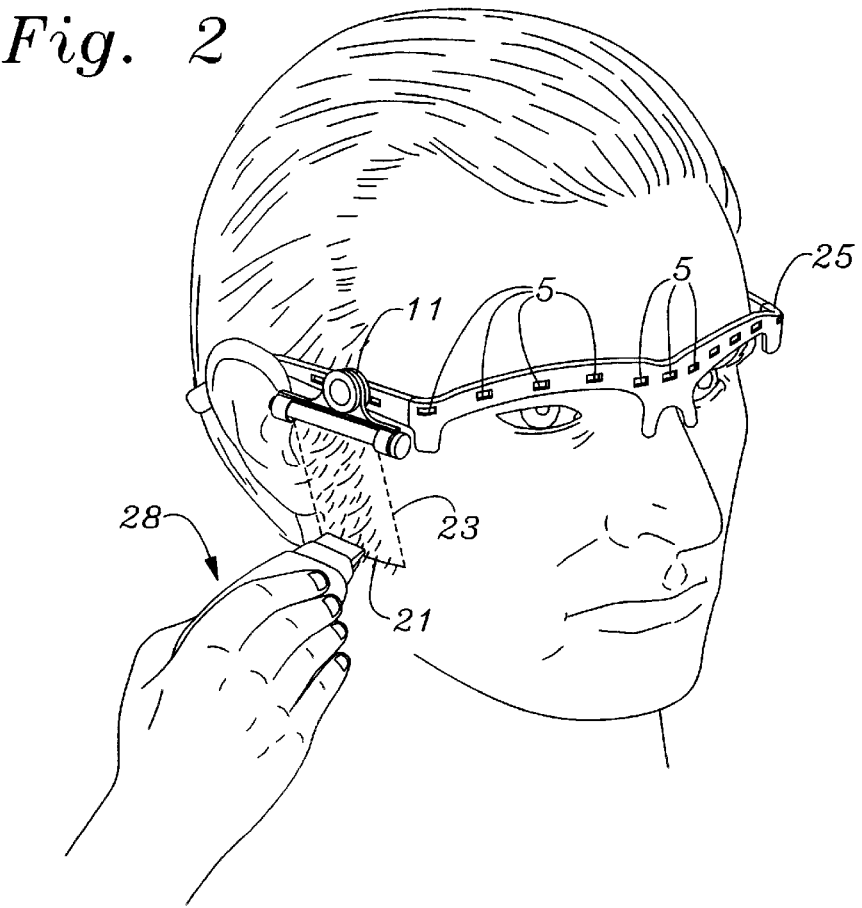
FIG. 2 is a side view of the embodiment of FIG. 1 illustrating as an example use as possible hair trimmer.

FIG. 2 shows one of the light means 11 secured to a side slot 5 on one side of the head in use producing light line 21 having outside edge 23 with a hair trimmer 28. The other light means can be secured to the other side of the head [not shown in this view].

Figure 3:
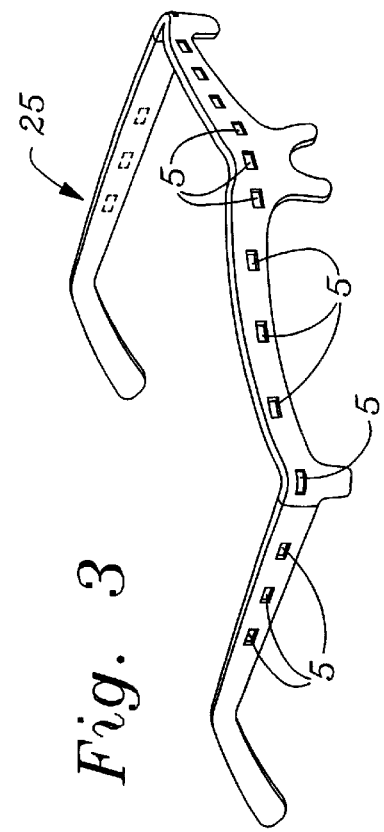
FIG. 3 is a perspective view of the frame.

FIG. 3 shows the frame 25 with slots 5.

Figure 4:
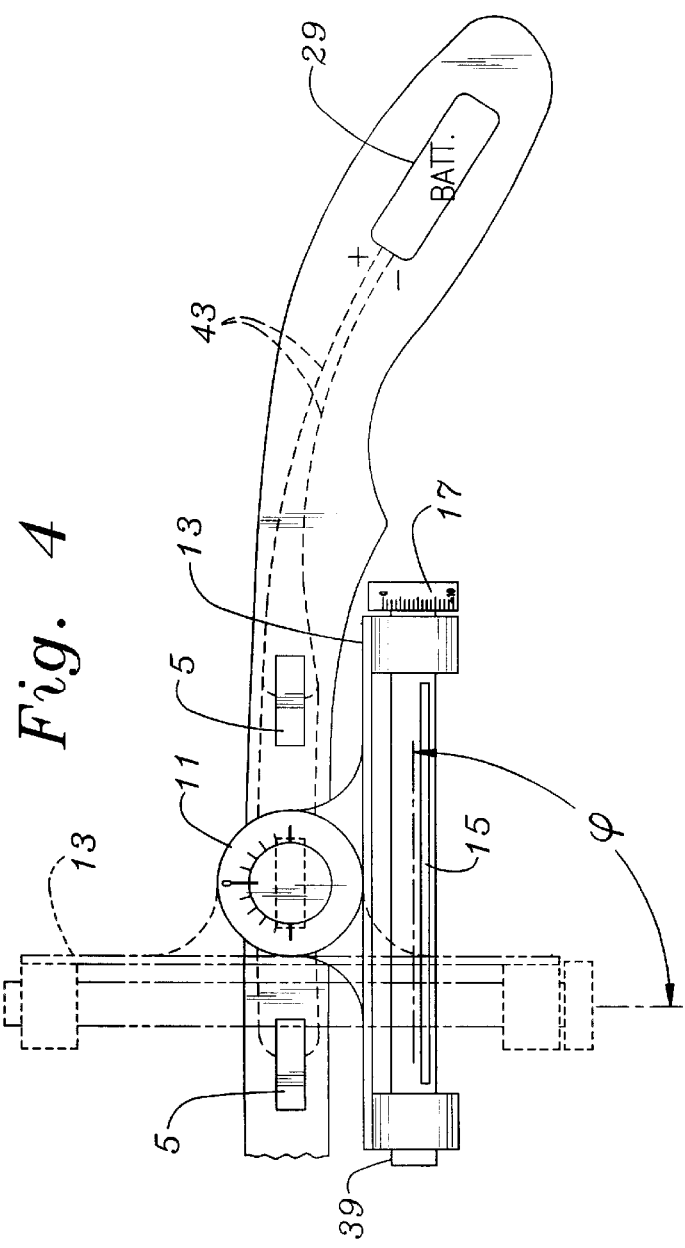
FIG. 4 is a side view of the frame illustrating slots for the light producing means.

FIG. 4 shows a bracket 13 to hold the light means, a wire holder 43 connecting battery 29 to the light means. The means comprises an elongated hollow cylinder 39 having an axial slit 15 through which the light passes. Light is produced by elongated light emitting means [shown as 41 in FIG. 8] disposed in the cylinder. A rotatable vertical dial 17 enables the cylinder 39 to be rotated to set the length of light.

Figure 5:
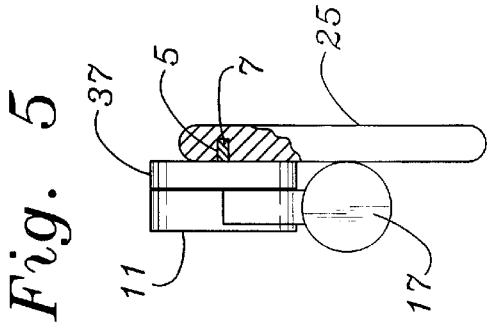
FIG. 5 is a cross section of the frame with the light producing means placed in a slot.
Figure 7:
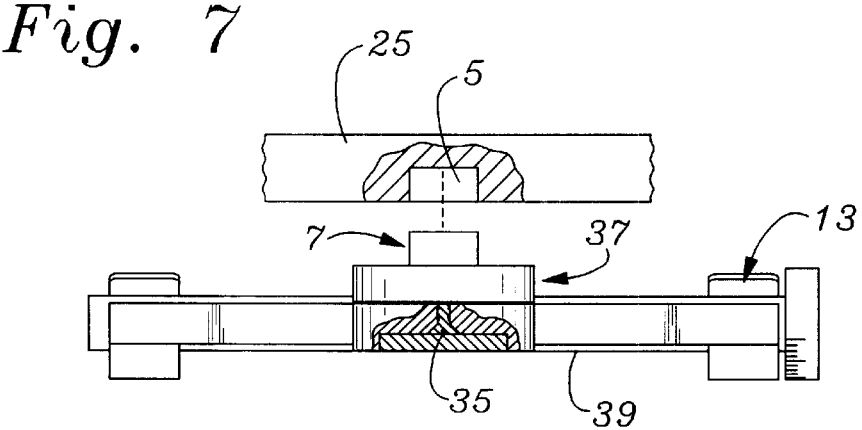
FIG. 7 is a top view of FIG. 5.

FIGS. 5 and 7 shows the frame 25 with a tab 7 connected to the base 37 and fitting into slot 5. Bracket 13 holds the cylinder 39. Screw 35 secures the base to the cylinder 39.

Figure 6:
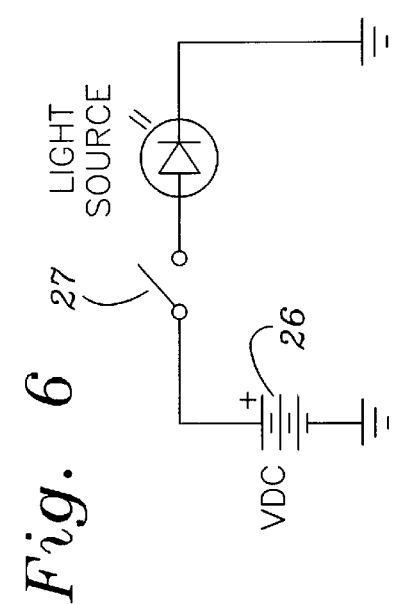
FIG. 6 illustrates two alternative electric sources, a battery and a wall outlet.

FIG. 6 shows the alternative arrangements of using a battery 26 or wall outlet together with an on-off switch 27 in energizing the light source.

Figure 8:
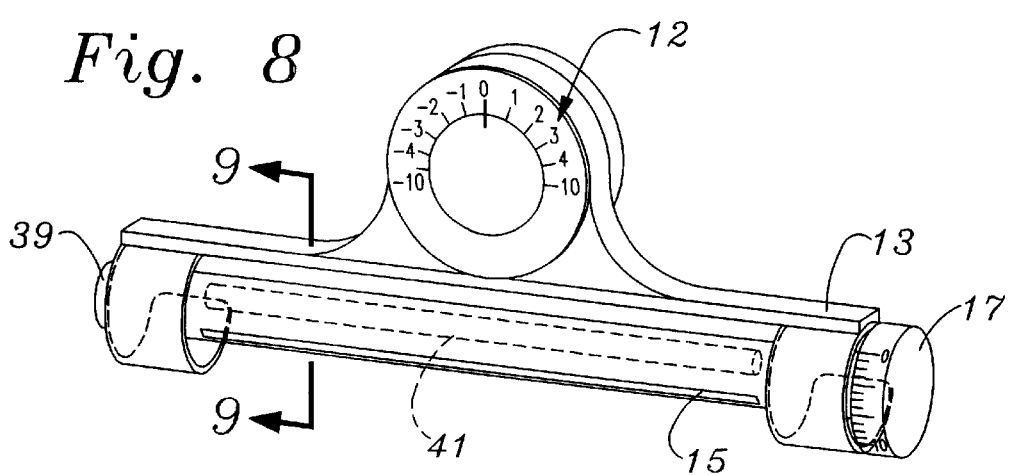
FIG. 8 illustrates the horizontal and vertical dials for setting inclination and length on the preferred embodiment of the invention.

FIG. 8 shows the horizontal dial 12 and the vertical dial 17 for setting inclination and length on the device.

Figure 9:
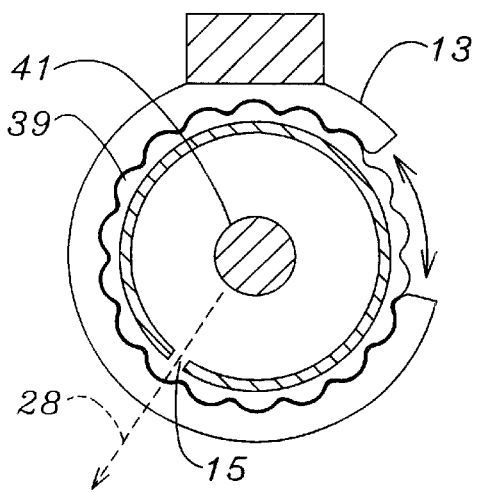
FIG. 9 is a cross sectional view of a portion of the structure of FIG. 8.

FIG. 9 shows the cylinder 39, light source 41, bracket 13, slit 15 and emission of light 28.

While the invention has been described with particular reference to the drawings and detailed description, the protection solicited is to be limited only by the claims which follow.

What is claimed is:

1. A device adapted for use with the head of a user, the user having a face with a nasal bone and ears, said device comprising:

a frame for resting on top of said bone and said ears, said frame having oppositely disposed horizontal ear pieces and a horizontal nose piece extending between and secured to said ear pieces;

at least one elongated hollow cylinder having an elongated axially extending slot which extends from the interior to the exterior of the cylinder, said cylinder containing an elongated light source which when electrically energized projects a reference line of light through said slot;

first means to energize said source;

an attachment for connecting said cylinder to one of said pieces; and second means secured to said cylinder for manually rotating the cylinder into a selected position at which said reference line is non-permanently placed upon said face without marking the face in any manner.

2. The device of claim 1 wherein said cylinder is disposed horizontally and said second means rotates the cylinder into said selected position in the horizontal plane.

3. The device of claim 1 wherein said cylinder is disposed vertically and said second means rotates the cylinder in said selected position in the vertical plane.

4. The device of claim 1 wherein there are two cylinders and two attachments, each cylinder being connected by its corresponding attachment to a different one of said pieces.

* * * * *

UNITED STATES PATENT AND TRADEMARK OFFICE
CERTIFICATE OF CORRECTION

PATENT NO.    : 6,553,680 B2                                             Page 1 of 1
DATED         : April 29, 2003
INVENTOR(S)   : Kamran Vazdi It is certified that error appears in the above-identified patent and that said Letters Patent is hereby corrected as shown below:

<u>Title page,</u>
Item [75], Inventor, should read -- Kamran Yazdi --.

Signed and Sealed this

Thirtieth Day of August, 2005

JON W. DUDAS
*Director of the United States Patent and Trademark Office*